(12) United States Patent
Chen et al.

(10) Patent No.: US 8,021,516 B2
(45) Date of Patent: Sep. 20, 2011

(54) USE OF WATER-SOLUBLE POLYMER COMPLEXES IN AQUEOUS SYSTEMS

(75) Inventors: Shih-Ruey T Chen, Pittsburgh, PA (US); Valentino L. DeVito, Pittsburgh, PA (US); Kevin W. Frederick, Evans City, PA (US)

(73) Assignee: WSP Chemicals & Technology, LLC, Ambridge, PA (US)

( * ) Notice: Subject to any disclaimer, the term of this patent is extended or adjusted under 35 U.S.C. 154(b) by 124 days.

(21) Appl. No.: 12/418,659

(22) Filed: Apr. 6, 2009

(65) Prior Publication Data

US 2009/0188639 A1 Jul. 30, 2009

Related U.S. Application Data

(62) Division of application No. 11/087,097, filed on Mar. 22, 2005, now Pat. No. 7,514,007, which is a division of application No. 10/122,764, filed on Apr. 15, 2002, now Pat. No. 7,001,953.

(60) Provisional application No. 60/284,043, filed on Apr. 16, 2001.

(51) Int. Cl.
*D21H 21/10* (2006.01)
*D21H 17/24* (2006.01)
*D21H 17/33* (2006.01)

(52) U.S. Cl. ............... 162/164.1; 162/164.3; 162/164.6; 162/168.1; 162/168.5; 162/168.7; 162/175; 162/177; 162/178

(58) Field of Classification Search ............... 162/164.1, 162/164.3, 164.6, 168.1, 168.2, 168.3, 168.5, 162/168.7, 175, 177, 178
See application file for complete search history.

(56) References Cited

U.S. PATENT DOCUMENTS

| | | | |
|---|---|---|---|
| 3,280,218 A | 10/1966 | Endsley et al. | |
| 3,755,159 A | 8/1973 | Nagy | |
| 3,770,673 A | 11/1973 | Slagel et al. | |
| 3,891,580 A | 6/1975 | Morris et al. | |
| 4,028,290 A | 6/1977 | Reid | |
| 4,105,605 A | 8/1978 | Cottrell et al. | |
| 4,464,523 A | 8/1984 | Neigel et al. | |
| 4,699,951 A | 10/1987 | Allenson et al. | |
| 4,703,801 A | 11/1987 | Fry et al. | |
| 5,108,622 A | 4/1992 | Liao et al. | |
| 5,213,693 A | 5/1993 | McGrow et al. | |
| 5,334,287 A * | 8/1994 | Hartmann et al. | 162/175 |
| 5,374,336 A * | 12/1994 | Lin et al. | 162/168.3 |
| 5,387,318 A | 2/1995 | Liao et al. | |
| 5,575,924 A | 11/1996 | Bair et al. | |
| 5,624,570 A | 4/1997 | Hassick | |
| 5,644,049 A | 7/1997 | Giusti et al. | |
| 5,658,993 A | 8/1997 | Denzinger et al. | |
| 5,693,034 A | 12/1997 | Buscemi et al. | |
| 5,800,719 A | 9/1998 | Sutman et al. | |
| 5,906,750 A | 5/1999 | Haase | |
| 5,925,379 A | 7/1999 | Mandeville, III et al. | |
| 7,001,953 B2 | 2/2006 | Chen et al. | |

FOREIGN PATENT DOCUMENTS

| | | |
|---|---|---|
| EP | 0359996 A2 | 3/1990 |
| GB | 2112005 | 7/1983 |

\* cited by examiner

*Primary Examiner* — Eric Hug
*Assistant Examiner* — Peter Chin
(74) *Attorney, Agent, or Firm* — Blynn L. Shideler; Krisanne Shideler; BLK Law Group

(57) ABSTRACT

A water-soluble interjacent complex that includes a first water-soluble polymer and one or more water-soluble monomers polymerized to form a second water-soluble polymer in the presence of the first water-soluble polymer. The water-soluble interjacent complex forms a solution in water that is free of insoluble polymer particles. The interjacent complexes may be used to treat a waste sludge by adding an effective amount thereof to the waste sludge. The interjacent complexes may also be used in making paper by adding an effective amount thereof to a pulp or a forming sheet at a suitable location on a paper making machine. The interjacent complexes may further be used as a rheology modifier in aqueous systems by adding an effective amount thereof to an aqueous medium to effect a desired viscosity, rheology, or flow curve property.

12 Claims, No Drawings

USE OF WATER-SOLUBLE POLYMER COMPLEXES IN AQUEOUS SYSTEMS

CROSS-REFERENCE TO RELATED APPLICATIONS

This application is a Division of application. Ser. No. 11/087,097, now U.S. Pat. No. 7,514,007 filed Mar. 22, 2005 and entitled "Use of Water-Soluble Polymer Complexes in Aqueous Systems," which is a Division of application. Ser. No. 10/122,764, now U.S. Pat. No 7,001,953, filed Apr. 15, 2002 and entitled "Water-Soluble Polymer Complexes," which claimed the benefit of U.S. Provisional Patent Application Ser. No. 60/248,043, filed April 16, 2001, and entitled "Water-soluble Polymer Complexes," all of which are herein incorporated by reference.

BACKGROUND OF THE INVENTION

1. Field of the Invention

The present invention relates to novel polymer compositions and methods for using such compositions. In general terms, the polymer compositions of the present invention are believed to be useful in water treatment in paper manufacture and as a rheology modifier.

2. Brief Description of the Prior Art

An interpenetrating polymer network ("IPN"), is an intimate combination of two polymers, both in network form, at least one of which is synthesized in the immediate presence of the other. In an IPN, at least one of the two polymers is crosslinked and the other may be a linear polymer (not crosslinked). The term IPN has been variously used to describe materials where the two polymers in the mixture are not necessarily bound together, but the components are physically associated.

U.S. Pat. No. 5,925,379 to Mandeville, III et al. discloses a method for removing bile salts from a patient, where a polymer network composition, which includes a cationic polymer is administered to the patient. The polymer network composition can include an interpenetrating polymer network, where each polymer within the network is crosslinked or an interpenetrating polymer network, where at least one polymer within the network is not crosslinked. Crosslinking the polymers renders the polymers non-adsorbable and stable. The polymer network composition does not dissolve or otherwise decompose to form potentially harmful byproducts and remains substantially intact so that it can transport ions out of the body following binding of bile acids.

U.S. Pat. No. 5,693,034 to Buscemi et al. discloses an angioplasty catheter that includes a composition coating on a distal end. The coating composition includes the reaction product of vinyl monomers polymerized to form a crosslinked polymer that adheres to the surface of the device in the presence of an uncrosslinked linear, water-soluble, hydrophilic hydrogel.

U.S. Pat. No. 5,644,049 to Giusti et al. discloses a biomaterial that includes an IPN. The IPN includes an acidic polysaccharide, such as hyaluronic acid and a non-toxic, non-carcinogenic synthetic polymer. The synthetic polymer may be crosslinked or grafted onto the acidic polysaccharide. The crosslinking or grafting is achieved using compounds capable of generating radicals or via functional groups on the acidic polysaccharide and the synthetic chemical polymer.

As the IPN examples described above illustrate, an IPN includes at least one crosslinked polymer with one or more other polymers, which may or may not be crosslinked in intimate combination with each other. When water-soluble polymers are included in the IPN, the resulting IPN is water dispersible, but it does not dissolve in water. While the use of an IPN may provide useful combinations of properties, its water insolubility can be a detriment in many end use applications.

U.S. Pat. No. 4,028,290 to Reid discloses a complex mixture of crosslinked grafted polysaccharide and acrylamide copolymers that have increased water-absorbing and binding capacity. The copolymers are prepared by reacting a polysaccharide, such as cellulose or starch, with acrylamide using a bisulfite-persulfate-ferrous ammonium sulfate grafting initiator.

U.S. Pat. No. 4,703,801 to Fry et al. discloses a graft polymer that has a backbone derived from lignin, lignite, derivatized cellulose, or synthetic polymers, such as polyvinyl alcohol, polyethylene oxide, polypropylene oxide, and polyethyleneimine, and pendant grafted groups that include homopolymers and copolymers of 2-acrylamido-2-methylpropanesulfonic acid, acrylonitrile, N,N-dimethylacrylamide, acrylic acid, N,N-dialkylaminoethylmethacrylate, and their salts. The graft copolymers are prepared by reacting the backbone polymer with ceric salts and a persulfate-bisulfite redox system in the presence of the selected monomers. The graft copolymers are useful in cementing compositions for use in oil, gas, water, and other well cementing operations and impart improved fluid loss capabilities.

U.S. Pat. No. 4,464,523 to Neigel et al. discloses graft copolymers of cellulose derivatives and N,N-diallyl,N-N-dialkyl ammonium chlorides or bromides, prepared using a dry or substantially solvent-free system. The preparation includes impregnating a concentrated aqueous solution of the N,N-diallyl-N,N-dialkyl ammonium halide, water-soluble surfactant, and redox catalyst onto the dry cellulose substrate, heating the reaction mass for sufficient time to achieve polymerization and then drying.

As described above, graft copolymers of polysaccharide and cellulosic backbone polymers are generally prepared by reacting portions of the backbone polymer with a redox catalyst generally including a ceric or ferrous salt to generate one or more free radicals. The free radicals on the backbone polymer then react with the monomers that are present to literally grow in graft polymer from the backbone polymer.

Graft copolymers differ from IPNs in that a first polymer acts as a substrate onto which another polymer is added, or a site on the first polymer is involved in initiating polymerization to form a pendant polymer arm. Graft copolymers can readily be formed from polysaccharide or cellulosic backbones using methods well known in the art. Examples of such methods include the ceric salt redox method (U.S. Pat. No. 3,770,673 to Slagle et al.) and graft initiation using formaldehyde and sodium metabisulfite (U.S. Pat. No. 4,105,605 to Cottrell et al.). In order to achieve a high degree of grafting, heavy metal ions, such as cerium IV or ferrous, or reagents, such as formaldehyde, are used to augment the grafting reaction. In many cases, the presence of such materials in a copolymer is undesirable because they are considered by many to be cancer causing agents in humans as well as environmentally harmful.

Further, graft copolymers are limited in the functional properties that they can provide. For example, the graft copolymer of U.S. Pat. No. 4,464,523 to Neigel et al. has highly charged cationic arms and a neutral backbone. The possible polymer confirmations that allow such a polymer to interact with a substrate are limited compared to a linear polymer. This limitation results in inferior performance when such a polymer is required to adsorb onto a substrate, for example, in waste water treatment or paper making applications.

Mixtures of polymers have been used in waste water treatment applications. For example, U.S. Pat. No. 4,699,951 to Allenson et al. discloses a polymer admixture that includes a low molecular weight cationic polymer and a high molecular weight cationic copolymer of acrylamide for treating and clarifying waste waters contaminated with oily waste and dispersed solids. U.S. Pat. No. 5,213,693 to McGrow et al. discloses treating sewage sludge and other organic suspensions for filter press or belt press dewatering using a dry blend of a low molecular weight cationic polymer and a high molecular weight cationic copolymer of acrylamide. U.S. Pat. No. 5,624,570 to Hassick discloses a method for treating laundry waste by sequentially adding a low molecular weight cationic polymer and a high molecular weight cationic copolymer of acrylamide to the waste stream. U.S. Pat. No. 5,906,750 to Haase discloses a method for the dewatering of biological sludge that has been digested by a thermophilic digestion process that includes sequentially adding a low molecular weight cationic polymer and a high molecular weight cationic copolymer of acrylamide to the biological sludge.

Unfortunately, physical mixtures of low molecular weight cationic polymers and high molecular weight cationic copolymers of acrylamide are not stable over time, as they tend to separate into two phases. Dry blends of such polymers are also problematic in that they are difficult to make down into a solution and readily adsorb moisture, which leads to clumping of the dry powder.

As the above examples demonstrate, however, in many uses for water-soluble polymers, it is desirable for the water-soluble polymer to adsorb onto a suspended solid surface from an aqueous solution to neutralize the surface charge, promote coagulation and/or flocculation of the solids, or to stabilize the suspension. Because an IPN is a water insoluble material, it is not able to provide these types of polymer-surface interations. Further, graft copolymers do not provide adequate performance in such applications, and physical blends of polymers often lack the requisite shelf life required to be useful commercially.

It would, therefore, be desirable to provide a material that is able to combine the favorable properties of two or more polymers, without resorting to the formation of a crosslinked matrix. Such a material should be easily prepared, easily used, and stable, i.e., not separate over time.

SUMMARY OF THE INVENTION

The present invention is directed to complexes of water-soluble polymers with other water-soluble polymers. The water-soluble polymer-polymer complex includes a first water-soluble polymer (a host polymer) and one or more water-soluble monomers polymerized to form a second water-soluble polymer (an intercalated polymer) in the presence of the first water-soluble polymer. The water-soluble polymer-polymer complex (interjacent complex) forms a solution in water that is free of insoluble polymer particles and maintains one uniform phase after standing at ambient conditions for at least three months.

The polymer-polymer complexes of the present invention may be used to treat a waste sludge. The waste treatment method includes adding an effective amount of the present water-soluble polymer-polymer complex to the waste sludge.

The present invention is also directed to a method of making paper. The present paper-making method includes adding the present polymer-polymer complex to a pulp or a forming sheet at a suitable location on a paper making machine.

The polymer-polymer complexes may further be used as a rheology modifier in aqueous systems. The polymer-polymer complex is used to increase the viscosity of an aqueous medium by adding an effective amount of the present polymer-polymer complex to the aqueous medium to effect a desired viscosity, rheology, or flow curve property.

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used herein, the term "substantially free" is meant to indicate that a material can be present in an incidental amount or that a particular occurrence or reaction only takes place to an insignificant extent, which does not effect desired properties. In other words, the material is not intentionally added to an indicated composition, but may be present at minor or inconsequential levels, for example, because it was carried over as an impurity as part of an intended composition component.

As used herein, the terms "(meth)acrylic" and "(meth)acrylate" are meant to include both acrylic and methacrylic acid derivatives, such as the corresponding alkyl esters often referred to as acrylates and (meth)acrylates, which the term "(meth)acrylate" is meant to encompass.

As used herein, the term "active basis" refers to a concentration of additive based on the active solids in the stock solution.

As used herein, the term "effective amount" refers to that amount of a composition necessary to bring about a desired result, such as, for example, the amount needed obtain a desired viscosity in an aqueous system.

As used herein, the term "polymer" is meant to encompass oligomer, and includes, without limitation, both homopolymers and copolymers.

As used herein, the phrase components "are different from each other" refers to components which do not have the same chemical structure as other components in the composition.

As used herein, the term "host polymer" refers to a polymer that is present during a polymerization reaction, but does not participate in initiating the polymerization reaction. The term "intercalated polymer" refers to the polymer that is formed in the presence of the host polymer.

As used herein, the terms "interjacent complex" and "polymer-polymer complex" refer to two polymers that are different from each other, and in intimate contact with each other. The interjacent or polymer-polymer complex is prepared by polymerizing monomers to form a polymer in the presence of a host polymer as described below. The polymer-polymer complex is substantially free of grafting, which occurs only to the extent that chain transfer reactions to the host polymer occur.

As used herein, the term "water-soluble," when used in relation to polymers and polymer-polymer complexes, refers to polymers and polymer-polymer complexes that form a solution in water that is free of insoluble polymer particles. The determination that a solution is free of insoluble polymer particles can be made using conventional light scattering techniques or by passing the solution through a sufficiently fine filter screen capable of capturing insoluble polymer particles. As a non-limiting example, an aqueous solution containing 5 percent by weight of a polymer or interjacent complex can be prepared and poured through a U.S. Standard Sieve No. 100 (150 µm), and no particles are left on the screen. Alternatively, the turbidity of an aqueous solution containing 5 percent by weight of a polymer or interjacent complex, at a pH of from 5-9, may be measured using a turbidimeter or nephelometer. A reading of less than 20 nephelometric turbidity units (NTU) indicates the water-solubility of the polymer of interjacent complex.

As used herein, the terms "branching" and "branched polymers" refer to the arms of polymers that have a main backbone with arms extending therefrom, are not interconnected with other polymer molecules, and are water-soluble. Polymers that contain branching are distinguished from crossliked polymers in that crosslinked polymers are polymers that are branched and interconnected with other polymer molecules to the point that they form a three-dimensional network and are not water-soluble, while branched polymers retain their water solubility.

As used herein, the phrase "no visible phase separation" refers to the homogenous nature of the present interjacent complexes. "No visible phase separation" refers to solutions containing two or more polymers that maintain a single uniform phase after standing at ambient conditions for at least three months.

The present invention is directed to novel water-soluble interjacent complexes. In particular, the present invention is directed to water-soluble interjacent complexes prepared by polymerizing one or more water-soluble ethylenically unsaturated polymerizable monomers in the presence of a host polymer. The resulting water-soluble interjacent complex forms a solution in water that is free of insoluble polymer particles.

Any ethylenically unsaturated polymerizable monomer can be used in the present invention, so long as the resulting interjacent complex is water-soluble. Preferred monomers are those that promote water solubility or dispersibility. In this regard, preferred monomers include, but are not limited to, one or more of the following monomers; cationic monomers, such as acrylamidopropyltrimethyl ammonium chloride (APTAC), methacrylamidopropyltrimethyl ammonium chloride (MAPTAC), diallyl dimethyl ammonium chloride (DADMAC), acryloyloxyethyl trimethyl ammonium chloride (AETAC), and methacryloyloxyethyl trimethyl ammonium chloride (METAC); anionic monomers, such as 2-acrylamido-2-methylpropane sulfonic acid (AMPSA), 2-methacrylamido-2-methylpropane sulfonic acid (MAMPSA), sulfonated styrene, and vinyl sulfonic acid; allyl ether sulfonic acids, such as propane sulfonic acid allyl ether, methallyl ether phenyl sulfonates, (meth)acrylic acid, maleic acid, itaconic acid, n-(meth)acrylamidopropyl,n,n-dimethyl, amino acetic acid, n-(meth)acryloyloxyethyl,n,n-dimethyl, amino acetic acid, n-(meth)acryloyloxyethyl,n,n-dimethyl,amino acetic acid, crotonic acid, (meth) acrylamidoglycolic acid, and 2-(meth)acrylamido-2-methylbutanoic acid; nonionic monomers, such as $C_1$-$C_{22}$ straight or branched chain alkyl or aryl (meth)acrylate, a $C_1$-$C_{22}$ straight or branched chain n-alkyl or aryl (meth)acrylamide, acrylamide, methylacrylamide, n-vinylpyrrolidone, vinyl acetate, ethoxylated, and propoxylated (meth)acrylate, hydroxy functional (meth)acrylates, such as hydroxyethyl (meth)acrylate and hydroxypropyl(meth)acrylate, n,n-dimethyl(meth)acrylamide, styrene and styrene derivatives, $C_1$-$C_{22}$ straight or branched chain alkyl, or aryl allyl ethers.

The interjacent complexes of the present invention are formed by polymerizing one or more of the above-described monomers to form an intercalated polymer in the presence of a host polymer. The host polymer can be a synthetic polymer, such as those produced by free radical polymerization or condensation polymerization, or it may be a natural polymer, such as a natural gum, a starch, a modified starch, a cellulosic, a modified cellulosic, a water-soluble natural gum, water-soluble modified natural gums, proteins, or protein derivatives. Examples of host polymers that can be used in the present invention include, but are not limited to, water-soluble vinyl polymers, water-soluble olefin containing copolymers, water-soluble polyacrylates, water-soluble polyamides, water-soluble polyesters, water-soluble polyurethanes, xanthan gums, sodium alginates, galactomanans, carageenan, gum arabic, cellulose and its derivatives, such as hydroxyethyl cellulose and hydroxypropyl cellulose, starch and its derivatives, guar and its derivatives, proteins and their derivatives, water-soluble poly(meth)acrylates, water-soluble polyamides, water-soluble polyesters, water-soluble polyurethanes, water-soluble poly(vinyl alcohol), water-soluble poly (vinyl amine), water-soluble poly(ethylene imine), water-soluble amine/epihalohydrin polyamines, water-soluble poly(meth)acrylamide, water-soluble (meth) acrylamide copolymers, water-soluble poly(meth)acrylic acid, water-soluble copolymers of (meth)acrylic acid, poly (diallyl dimethyl ammonium halides), copolymers of diallyl dimethyl ammonium halides, water-soluble vinyl pyrrolidone, water-soluble copolymers of vinyl pyrrolidone, poly (meth)acrylamidopropyltrimethyl ammonium halides, copolymers of (meth)acrylamidopropyltrimethyl ammonium halides, poly(meth)acryloyloxyethyltrimethyl ammonium halides, copolymers of (meth)acryloyloxyethyltrimethyl ammonium halides, poly(meth)acryloyloxyethyltrimethyl ammonium methyl sulfate, and copolymers of (meth)acryloyloxyethyltrimethyl ammonium methyl sulfate.

The molecular weight (Mw) of the host polymer and the intercalated polymer will both be at least 1,000, in some cases, at least 5,000, in other cases, at least 10,000, in some instances, at least 20,000, and in other instances, at least 25,000 or 50,000. On occasion, the molecular weight of the host polymer and the intercalated polymer will both be not more than 10,000,000, in some cases, not more than 5,000, 000, in other cases, not more than 2,500,000, in some instances, not more than 1,000,000, and in other instances, not more than 500,000. The actual molecular weight of the host polymer and the intercalated polymer is determined based on the intended use and properties desired in the interjacent complex. The molecular weight of the host polymer and the intercalated polymer may be any value or any range of values inclusive of those stated above. The molecular weight ("Mw") of the host polymer and the intercalated polymer may be determined by viscometry in a Ubbelhhde Capillary Viscometer at 0.05% by weight concentration of the host polymer or intercalated polymer in 1M NaCl solution, at 30° C., pH 7. The reduced viscosity measured under such conditions may range from 0.1 to 20 dl/g, in some cases, 0.25 to 15 dl/g, in other cases, 0.5 to 12.5 dl/g, and in other instances, 1 to 10 dl/g. Alternatively, gel permeation chromatography (GPC) using appropriate standards can be used to determine molecular weight, in which case the Mw value is used as the molecular weight measurement.

A class of polymers that is particularly useful in the present invention as host polymers includes those referred to as polyquaterniums. Preferred polyquaterniums include those described in the International Cosmetic Ingredient Dictionary, published by the Cosmetic, Toiletry, and Fragrance Association (CTFA), 1101 17$^{th}$ Street, N.W., Suite 300, Washington, D.C. 20036. Examples of such polyquaterniums include, but are not limited to, (1) the polymeric quaternary ammonium salt of hydroxyethyl cellulose reacted with a trimethyl ammonium substituted epoxide, referred to as Polyquaternium-10; (2) the quaternary ammonium derivative of hydroxypropyl guar, referred to as guar hydroxypropyltrimonium chloride; (3) the copolymer of hydroxyethylcellulose and DADMAC referred to as Polyquaternium-4; (4) the copolymer of acrylamide and METAMS, referred to as Polyquaternium-5; (5) the homopolymer of DADMAC, referred to as Polyquaternium-6; (6) The copolymer of acrylamide and DADMAC, referred to as Polyquaternium-7; (7) the copolymer of vinyl pyrrolidone and METAMS, referred to as Polyquaternium-11; (8) the homopolymer of METAMS, referred to as Polyquaternium-14; (9) the copolymer of methacrylamide and METAMS, referred to as Polyquaternium-15; (10) the polymeric quaternary ammonium salt of hydroxyethyl cellulose reacted with a lauryl dimethyl ammonium substituted epoxide, referred to as Polyquaternium-24; (11) the copolymer of vinyl pyrrolidone and MAPTAC, referred to as Polyquaternium-28; (12) the copolymer of acrylamide and METAC, referred to as Polyquaternium-32; (13) the copolymer of acrylamide and AETAC, referred to as Polyquaternium-33; (14) the copolymer of butylmethacrylate, dimethylaminoethylmethacrylate, and METAMS, referred to as Polyquatemium-36; (15) the homopolymer of METAC referred to as Polyquaternium-37; (16) the copolymer of METAMS, methyl methacrylate and hydroxyethylmethacrylate referred to as Polyquaternium-45; (17) the homopolymer of MAPTAC referred to as polymethacrylamidopropyltrimonium chloride; (18) Hydroxypropyl trimethyl ammonium chloride ether derivatives of starch, as generally described by the CAS Registry Number 5670-58-6, the starch of which can be derived from a variety of natural sources such as corn, potato, rice, tapioca, wheat, or other sources; (19) the copolymer of DADMAC and acrylic acid, referred to as Polyquaternium-22, (20) the copolymer of DADMAC, acrylic acid and acrylamide, referred to as Polyquaternium-39; and (21) the copolymer of MAPTAC, acrylic acid, and methyl(meth)acrylate, referred to at Polyquaternium-47.

One or more host polymers may be used to prepare the present water-soluble interjacent complex. The host polymer is present during the polymerization and formation of the intercalated polymer. As such it is present at a level of at least 0.01 wt. %, in some cases, at least 0.1 wt. %, in other cases, at least 0.5 wt. %, in some instances, at least 1.0 wt. % and in other instances, at least 5 wt. % based on the total weight of monomer and host polymer in the composition of the interjacent complex. The host polymer is present at a level that will allow its beneficial properties to be ascertainable. The level of the host polymer in the interjacent complex can be up to 95 wt. %, in some cases, up to 75 wt. %, in other cases, up to 50 wt. %, in some instances, up to 25 wt. % and in other instances up to 10 wt. % based on the total weight of monomer and host polymer in the composition of the interjacent complex. The maximum limit for the host polymer is determined by the properties desired in the interjacent complex and the molecular weight of the host polymer. The host polymer level is not so high as to make the polymerization medium too highly viscous as to deter thorough mixing of the host polymers and monomers for the intercalated polymer. The amount of host polymer in the present interjacent complex can be any level or range of the levels recited above.

In an embodiment of the present invention, the interjacent complex is prepared in the presence of one or more of the above-mentioned host polymers. The polymerization is carried out using a monomer composition including: (a) 0 to 100 mol %, typically, 5 to 90 mol %, in some cases, 10 to 75 mol %, and in other cases, 20 to 50 mol % of a cationic monomer; (b) 0 to 100 mol %, typically, 5 to 50 mol %, in some cases, 10-50 mol %, and in other cases, 20 to 45 mol % of an anionic monomer; (c) 0 to 100 mol %, typically, 10 to 90 mol %, in some cases, 15-75 mol %, and in other cases, 20 to 60 mol % of a nonionic monomer polymerized in the presence of the host polymer. In this embodiment (a), (b), and (c) are different from each other and the total mol % for (a), (b), and (c) is 100 mol %.

In a further embodiment, the present invention is directed to a water-soluble interjacent complex prepared by polymerizing a monomer mixture that includes: (a) a cationic monomer; (b) a sulfonic acid containing anionic monomer; (c) a carboxylic acid containing anionic monomer; and (d) a nonionic monomer in the presence of one or more of the above-mentioned host polymers.

When included, the cationic monomer is present in the intercalated polymer at a level of at least 5 mol %, in some cases, at least 10 mol %, in other cases, at least 15 mol %, and in some instances, at least 20 mol % based on the total monomer composition of the intercalated polymer. The cationic monomer promotes surface adsorption of the present interjacent complex onto solid particles being treated by the interjacent complex. When used, the level of cationic monomer in the intercalated polymer can be up to 95 mol %, in some cases, up to 85 mol %, in other cases, up to 75 mol %, and in some instances, up to 60 mol % based on the total monomer composition of the intercalated polymer. The amount of cationic monomer in the present intercalated polymer can be any level or range of the levels recited above.

When included, the sulfonic acid functional anionic monomer is included in the present intercalated polymer at a level of at least 1 mol %, in some cases, at least 5 mol %, in other cases, at least 7.5 mol %, and in some instances, at least 10 mol %. When included, the level of sulfonic acid functional anionic monomer is present in the intercalated polymer at up to 80 mol %, in some cases, to 70 mol %, in other cases, up to 60 mol %, and in some instances, up to 50 mol % based on the total monomer composition of the intercalated polymer. The amount of sulfonic acid functional anionic monomer in the intercalated polymer of the present invention may be any level or range of the levels recited above.

The carboxylic acid functional anionic monomer is optionally included in the intercalated polymer. When the carboxylic acid functional anionic monomer is included, it is included at a level of at least 1 mol %, in some cases, at least 5 mol %, in other cases, at least 10 mol %, and in some instances, at least 15 mol %. The level of carboxylic acid functional anionic monomer in the intercalated polymer can be up to 80 mol %, in some cases, up to 50 mol %, in other cases, up to 40 mol %, in some instances, up to 30 mol %, and in other instances, up to 25 mol % based on the overall intercalated polymer composition. The amount of carboxylic acid functional anionic monomer in the present intercalated polymer can be any level or range of levels recited above.

The nonionic monomer is optionally included in the intercalated polymer. When the nonionic monomer is included, it is included at a level of at least 5 mol %, in some cases, at least 10 mol %, in other cases, at least 15 mol %, and in some instances, at least 20 mol %. The nonionic monomer may promote hydrogen bonding between the present interjacent complex and the solids in an aqueous system. The level of nonionic monomer in the intercalated polymer can be up to 99 mol %, in some cases, 90 mol %, in other cases, up to 60 mol %, in some instances, up to 50 mol %, and in other instances, up to 45 mol % based on the overall intercalated polymer composition. The amount of nonionic monomer in the intercalated polymer can be any level or range of levels recited above.

In an embodiment of the present invention, when one or more nonionic monomers are included in the intercalated polymer, the intercalated polymer may include: (a) from 20 to 95 mol %, in some cases, 20 to 50 mol %, in other cases, 25 to 50 mol %, and in some instances, 30 to 45 mol % of a cationic monomer; (b) 0 to 80 mol %, in some cases, 5 to 40 mol %, in other cases, 5 to 30 mol %, and in some instances, 5 to 25 mol % of a sulfonic acid functional anionic monomer, (c) 0 to 55 mol %, in some cases, 5 to 50 mol %, in other cases, 10 to 45 mol %, and in some instances, 15 to 45 mol % of nonionic monomer; and (d) 0 to 25 mol %, in some cases, 5 to 25 mol %, in other cases, 10 to 25 mol %, and in some instances, 15 to 25 mol % carboxylic acid functional anionic monomer. The sum of the total amount of monomers in (a), (b), (c), and (d) is always 100 mol %.

Any suitable cationic monomer may be used to make the intercalated polymer of the present invention. Presently preferred cationic monomers include, but are not limited to, acrylamidopropyltrimethyl ammonium halide (APTAH), methacrylamidopropyltrimethyl ammonium halide (MAPTAH), diallyl dimethyl ammonium halide (DADMAH), acryloyloxyethyl trimethyl ammonium halide (AETAH), and methacryloyloxyethyl trimethyl ammonium halide (METAH). In an embodiment of the present invention, the halides are selected from chloride, bromide, and iodide.

Any suitable sulfonic acid containing anionic monomer may be used to make the intercalated polymer of the present invention. Presently preferred sulfonic acid containing anionic monomers include, but are not limited to, 2-acrylamido-2-methylpropane sulfonic acid (AMPSA), 2-methacrylamido-2-methylpropane sulfonic acid (MAMPSA), sulfonated styrene, vinyl sulfonic acid, allyl ether sulfonic acids, such as propane sulfonic acid allyl ether, and methallyl ether phenyl sulfonates.

In an embodiment of the present invention, the mol ratio of cationic monomer to sulfonic acid containing anionic monomer in the intercalated polymer ranges from 20:80 to 95:5, typically, from 25:75 to 75:25.

Any suitable nonionic monomer may be used to make the intercalated polymer of the present invention. Presently preferred nonionic monomers include, but are not limited to, $C_1$-$C_{22}$ straight or branched chain alkyl or aryl (meth)acrylate, a $C_1$-$C_{22}$ straight or branched chain n-alkyl or aryl (meth)acrylamide, acrylamide, methylacrylamide, n-vinylpyrrolidone, vinyl acetate, ethoxylated, and propoxylated (meth)acrylate, hydroxy functional (meth)acrylates, such as hydroxyethyl(meth)acrylate and hydrocypropyl(meth)acrylate, n,n-dimethyl(meth)acrylamide, styrene and styrene derivatives, $C_1$-$C_{22}$ straight or branched chain alkyl, or aryl allyl ethers.

Any suitable carboxylic acid containing anionic monomer may be used to make the intercalated polymer of the present invention. Preferred carboxylic acid containing monomers include, but are not limited to, (meth)acrylic acid, maleic acid, itaconic acid, N-(meth)acrylamidopropyl,N,N-dimethyl,amino acetic acid, N-(meth)acryloyloxyethyl, N,N-dimethyl, amino acetic acid, N-(meth)acryloyloxyethyl,N,N-dimethyl, amino acetic acid, crotonic acid, (meth)acrylamidoglycolic acid, and 2-(meth)acrylamido-2-methylbutanoic acid.

The interjacent complexes of the present invention provide several advantages when compared to physical blends of comparable polymers. The interjacent complexes provide a means of formulating with highly charged polymers in formulations that would otherwise be incompatible with such ingredients in the formulation. Solutions of the present interjacent complex demonstrate improved stability, i.e., less or no visible phase separation over time, than comparable physical blends or mixtures of comparable polymers. The interjacent complexes provide a means of delivering a highly charged polymer to the surface of dispersed solids in an aqueous system. Further, the combined action of the two polymers, as complexed herein, provide enhanced and synergistic performance and physical properties compared to physical blends or mixtures of comparable polymers.

The weight average molecular weight of the interjacent complex, as determined by viscometry, is at least 1,000, preferably from 10,000 to 10,000,000, more preferably from 25,000 to 8,000,000 and most preferably from 50,000 to 5,000,000. Alternatively, gel permeation chromatography (GPC) using appropriate standards can be used to determine molecular weight, in which case, the Mw value is used as the molecular weight measurement. The molecular weight (Mw) of the interjacent complex may be determined by viscometry in a Ubbelhhde Capillary Viscometer at 0.05% by weight concentration of the interjacent complex in IM NaCl solution, at 30° C., pH 7. The reduced viscosity measured under such conditions may range from 0.1 to 20 dl/g, in some cases, 0.25 to 15 dl/g, in other cases, 0.5 to 12.5 dl/g, and in other instances, 1 to 10 dl/g. Alternatively, gel permeation chromatography (GPC) using appropriate standards can be used to determine molecular weight, in which case, the Mw value is used as the molecular weight measurement.

The present interjacent complexes may be prepared by conventional solution polymerization techniques, or alternatively, by water-in-oil emulsion polymerization techniques. When prepared as a solution polymerization, the polymer and monomer(s) are combined in an aqueous solution, and the monomers are polymerized.

In an oil-in-water emulsion system, the host polymer and monomer(s) are combined in an aqueous solution and dispersed in a suitable hydrocarbon continuous phase to form discrete droplets dispersed within the hydrocarbon. A suitable initiator is then added to the water-in-oil emulsion, which is allowed to polymerize in either an adiabatic or isothermal mode. In an alternative embodiment, an oil soluble monomer can be added after the above-described polymerization step, and subsequently polymerized using a suitable initiator to form core-shell dispersed particles. In this alternative embodiment, the outer surface, or shell, of the particle contains the polymerized oil soluble monomer and the inner portion, or core, contains the interjacent complex.

In an embodiment of the present invention, the interjacent complex is formed via a solution polymerization. To prepare the present interjacent complex, the appropriate weights for the desired mol percentages of monomers, for example, cationic monomer, sulfonic acid containing anionic monomer, carboxylic acid containing anionic monomer, and nonionic monomer, together with one or more of the above-mentioned host polymers are charged to a glass reactor equipped with a stirring means. The desired total monomer concentration is generally about 10-30% by weight. The monomer mixture may then be adjusted to a pH of about 2.0 to about 6.5 with dilute NaOH, heated to about 55° C., and purged with nitrogen for at least thirty minutes. Polymerization is then initiated by adding $5 \times 10^{-2}$ mol % of sodium persulfate and $2.4 \times 10^{-3}$ mol % of sodium bisulfate. After the peak exotherm is reached, additional dilution water and sodium bisulfite are added to scavenge any residual monomer and to dilute the final product polymer solids. The use of ceric or ferrous ions is avoided so as to not promote grafting cations. In other words, the present polymerization is conducted in the substantial absence of ceric, ferrous or feric ions.

Regardless of the preparation process employed, the host polymer and the intercalated polymer can be polymers made using different manufacture techniques. For example, one polymer can be made using an adiabatic process, which will typically result in a wide molecular weight and polymer composition distribution. The other polymer can be prepared using an isothermal process, which will typically provide a polymer with a narrow molecular weight distribution. The resulting interjacent complex resulting from the combination of the two manufacturing processes results in unique properties for the resulting complex.

The intercalated polymer derived from polymerizing the above mentioned monomers in the presence of a host polymer may be branched by including suitable "crosslinking" monomers in the polymerization process. A crosslinking monomer is one or more monomers that have two or more sites of reactive unsaturation. Typically, a branching quantity of one or more monomers that have two or more sites of reactive unsaturation are used in addition to the above-described monomers to make the intercalated polymer. The branching quantity of the monomers having two or more sites of reactive unsaturation may be from 0.0001 to 0.1 mol %, in some cases, 0.001 to 0.09 mol %, in other cases, 0.01 to 0.075 mol % in some instances, 0.015 to 0.05 mol %, and in other instances, 0.02 to 0.03 mol % based on the total number of mols of monomers used to make the intercalated polymer.

Examples of monomers having two or more sites of reactive unsaturation that may be used in the present invention include, but are not limited to, ethylene glycol di(meth)acrylate, triethylene glycol di(meth)acrylate, tetraethylene glycol di(meth)acrylate, 1,3-butylene glycol di(meth)acrylate, trimethylolpropane tri(meth)acrylate, 1,4-butanediol di(meth) acrylate, neopentyl glycol di(meth)acrylate, 1,6-hexanediol di(meth)acrylate, pentaerythritol di(meth)acrylate, pentaerythritol tri(meth)acrylate, pentaerythritol tetra(meth) acrylate, glycerol di(meth)acrylate, glycerol allyloxy di(meth)acrylate, 1,1,1-tris(hydroxymethyl)ethane di(meth) acrylate, 1,1,1-tris(hydroxymethyl)ethane tri(meth)acrylate, 1,1,1-tris(hydroxymethyl)propane di(meth)acrylate, 1,1,1-tris(hydroxymethyl)propane tri(meth)acrylate, triallyl cyanurate, triallyl isocyanurate, triallyl trimellitate, diallyl phthalate, diallyl terephthalte, divinyl benzene, triallylamine, and methylenebis (meth) acrylamide.

Further, the interjacent complexes of the present invention may be purified, or provided in "narrow" molecular weight form, through art recognized methods of polymer fractionation by using poor solvents and/or non-solvents for the interjacent complex. Other methods of fractionating the interjacent complex include, but are not limited to, precipitation and membrane separation, including the use of crossflow membranes.

Reduced viscosity (dl/g) may be used as an approximate measure of the weight average molecular weight of the interjacent complexes of the present invention. The values may be determined using a Ubbelhhde Capillary Viscometer at 0.05% concentration of polymer in a 1M NaCl solution, pH 7, at 30 ° C. The resulting molecular weight value is calculated in accordance with methods well known in the art. The reduced viscosity of the interjacent complex of the present invention is from 0.1 to 20 dl/g, in many cases, 0.5 to 15 dl/g, preferably, 0.75 to 12.5 dl/g, and in some cases, 1 to 10 dl/g.

Not wishing to be bound to any single theory, it is believed that during the polymerization process, a minimal amount of grafting onto the host polymer may take place due to chain transfer to polymer reactions. However, the great bulk and majority of the host polymer molecules and polymer molecules formed during polymerization are not grafted, interlinked, or in any way covalently bonded to each other. Further, it is believed that the host polymer and the intercalated polymer form a structure where hydrophobic domains in the polymer molecules associate with each other, oppositely charged ionic or dipolar species in each polymer associate with each other as well as other forces, such as Van der Walls and hydrogen bonding, act to maintain the polymer molecules in intimate association with each other. These associations may mimic what is commonly observed in many interpenetrating polymer networks. The interjacent complex that is formed cannot be formed through physical mixing and does not phase separate on standing, dissociate on dilution, or physical manipulation of the interjacent complex. The polymer-polymer interactions and entanglements aid in stabilizing the interjacent complex that forms and minimizes the potential negative consequences that may occur due to, for example, poly salt formation. Laboratory experiments indicate that the two polymer components in the present interjacent complex cannot be separated by conventional separation techniques, indicating the unique structure that is formed between the two polymers.

The interjacent complexes of the present invention may be used to separate solids and dewater sludge in water treatment operations. Traditional organic flocculates are high to very high molecular weight polyelectrolytes that can be anionic, cationic, or nonionic in charge. With some exceptions, at least one of the host or intercalated polymers of the present interjacent complex flocculants will be a homopolymer or copolymer of acrylamide. Typical molecular weights for the acrylamide based polymer in the interjacent complex flocculant average 1,000,000 to 25,000,000. High molecular weight means long chains of molecules that have the capability of physically bridging from one microscopic particle to another.

The interjacent complex water treatment additives can be used with one or more coagulants. The most widely used coagulants are aluminum sulfate, aluminum chloride, ferric chloride, ferric sulfate, calcium oxide (lime), and magnesium oxide. Inorganic polymers of aluminum and iron that carry a positive charge are also widely used. The aluminum compounds are referred to as polyaluminum chloride and aluminumchlorohydrate when they are more fully neutralized.

Organic coagulants can also be used and are typically based on cationic polymers that contain quaternary nitrogen chemistry, examples of such include, but are not limited to, poly (DADMAC) and polyamines.

When used as a flocculent for water treatment, the host polymer can be a high molecular weight acrylamide based (co)polymer or a high charge density polyelectrolyte. The intercalated polymer comprises suitable monomers to enhance the performance and storage stability of the interjacent complex. Additionally, when forming the interjacent complex, an inorganic or organic coagulant or mixture thereof can be present and encased in the interjacent complex.

In an embodiment of the present invention, the host polymer is an organic coagulant polymer, and the intercalated polymer is an acrylamide based polymer flocculent. In a particular embodiment, the organic coagulant host polymer is one or more of amine/epihalohydrin polyamines, poly(diallyldimethyl ammonium halides), poly(ethylenimines), poly(meth)acryloyloxyethyltrimethyl ammonium halides, and poly(meth)acryloyloxyethyltrimethyl ammonium methyl sulfate; and the acrylamide based polymer is an anionic, nonionic, or cationic polyacrylamide.

The interjacent complex of the present invention provides superior separation and dewatering of waste sludge. The waste sludge may be a primary or secondary municipal sludge, thermophilic digested sludge, raw sewage sludge, oily waste sludges, sludges of dispersed solids, industrial waste sludges, sludges generated from paper mills, and laundry waste sludges. In particular, the interjacent complex of the present invention provides more efficient filter press or belt press dewatering.

The interjacent complexes of the present invention provide enhanced flocculation or removal of fine particles suspended in a liquid medium, forming stable aggregates called flocs. The interjacent complex flocculants of the present invention can be in solution, dry or water-in-oil emulsion form.

The interjacent complexes of the present invention can further be used in paper manufacture. When used in the manufacture of paper, the interjacent complex is added to at a suitable location on the paper machine to aid in forming the sheet and promoting dewatering of the formed sheet. These characteristics are generally described as formation and dewatering. The present interjacent complexes may also improve the wet and dry strength of the paper as one skilled in the art can appreciate.

When the interjacent complex of the present invention is utilized in paper manufacture, either the host polymer or the intercalated polymer will be a high molecular weight acrylamide based polymer. Typically, one or both of the polymer components of the interjacent complex will carry an ionic charge. The composition of each polymer will vary depending on the exact paper properties desired, the type of paper machine employed, the type of paper being produced, and the quality of the paper being produced.

In a particular embodiment of the present interjacent complex additive for paper manufacture, the host polymer is a cationic polymer, and the formed or polymerized polymer is a high molecular weight acrylamide based polymer. In this embodiment, the cationic polymer is one or more of amine/epihalohydrin polyamines, poly(diallyldimethyl ammonium halides), poly(ethylenimines), poly(meth)acryloyloxyethyltrimethyl ammonium halides, and poly(meth)acryloyloxyethyltrimethyl ammonium methyl sulfate, and the acrylamide based polymer is an anionic, nonionic, or cationic polyacrylamide.

The interjacent complexes of the present invention can further be utilized as viscosity and/or rheology modifiers.

When used as a viscosity or rheology modifier, an effective amount of the interjacent complex is added to an aqueous medium to effect desired viscosity, rheology, or flow curve characteristic. The present interjacent complexes can be used as viscosity or rheology modifiers in inks, caulks, grouts, adhesives, paints, and various coating compositions.

The present invention will further be described by reference to the following examples. The following examples are merely illustrative of the invention and are not intended to be limiting. Unless otherwise indicated, all percentages are by weight.

EXAMPLE 1

The ingredients in Table 1 were added to a 2-Liter Resin Kettle fitted with a condenser, stirrer, and thermocouple.

TABLE 1

| Ingredient | Charge (g) |
|---|---|
| Charge 1 | |
| Polyquaternium-7[1] | 237.3 |
| DADMAC[2] | 1076.9 |
| NaEDTA[3] | 0.75 |
| Charge 2 | |
| Sodium Persulfate | 4.1 |
| Deionized water | 25.4 |
| Charge 3 | |
| Deionized water | 409.7 |

[1]20 wt % aq. gel available as in-process WSPQ7,. WSP Chemicals & Technologies, Inc., Ambridge, Pa.
[2]64.8 wt. % solution in water available from Pearl River Polymer, Slidell, La.
[3]Tetrasodium N,N',N'',N'''-ethylene diamine tetra acetic acid Charge 1 was added to the Resin Kettle and heated to 80° C. with stirring until homogeneous (about 2 hours). Approximate concentration of DADMAC was 53.0% and Polyquaternium-7 is 3.6% by weight. Charge 2 was fed to the Resin Kettle at a rate of 0.064 ml/min for a period of 50 minutes. After about a 12 minutes the temperature of the solution began to rise indicating that polymerization had begun. The feed rate of charge 1 was decreased to 0.16 ml/min for a period of 20 minutes. The temperature of the reaction mix increased to about 110° C. and was maintained there due to reflux. The remainder of charge 1 was fed to the Resin Kettle at a rate of 0.32 ml/min (about 50 -60 minutes). The temperature was maintained between 100-105° C. Charge 3 was heated to at least 80° C., and maintained at this temperature with stirring for 40 minutes until a uniform mixture was formed. The solution was cooled to about 40° C. and 50 wt. % aqueous sodium hydroxide was added dropwise until the pH was between 6 -7. The resulting solution contained 39.7% poly(DADMAC) and 2.7% Polyquaternium-7. The solution remained uniform after standing at room temperature for three months. A 5 wt. % aqueous solution (active polymer basis) of the poly(DADMAC)—Polyquaternium-7 interjacent complex passed through a 100 mesh sieve (EW-59994-16, Cole-Parmer Instrument Company, Vernon Hills, Ill.) and left no insoluble polymer residue on the screen. The 5 wt. % solution was also measured for turbidity on a standard laboratory turbidimeter (Model 2100AN, Loveland, Col.) and measured less than 20 ntu.

EXAMPLE 2

The ingredients in Table 2 were added to a 2-Liter Resin Kettle fitted with a condenser, stirrer, thermocouple and nitrogen purge tube.

TABLE 2

| Ingredient | Charge (g) |
| --- | --- |
| Charge 1 | |
| Polyquaternium-11[4] | 240.1 |
| MEHQ[5] | 0.0016 |
| Deionized water | 227.6 |
| Charge 2 | |
| Acrylamide (50%) | 82.4 |
| DADMAC (64.8%) | 44.9 |
| NaEDTA | 0.28 |
| Charge 3 | |
| 2,2'-Azobis(2-methylpropionamide)dihydrochloride[6] | 0.2 |
| Deionized water | 5.0 |
| Charge 4 | |
| Deionized water | 130.0 |
| Sodium metabisulfite | 2.0 |

[4]20 wt % aqueous solution available as Gafquat ® 755N from International Specialty Products, Wayne, N.J.
[5]Methyl ester of hydroquinone
[6]Available as V-50 from Wako Chemicals USA, Inc., Dallas, TX.

Charge 1 was added to the Resin Kettle with mixing, heat was applied to aid in homogenizing the solution. Charge 2 was added to the Resin Kettle, heating was continued with stirring and a nitrogen sub-surface purge at about 3-5 scfh was started. Heating was continued to 60° C. and the nitrogen purge was maintained for at least 30 minutes. Charge 3 was added to the Resin Kettle. An exotherm was noticed after one or two minutes after which time the nitrogen purge was reduced to a blanket headspace flow of about 0.5 scfh. The reaction temperature peaked at about 75° C. The temperature was maintained for about two hours at which time charge 4 was added to the Resin Kettle with stirring and held at 75° C. for 30 minutes. The solution remained uniform after standing at room temperature for three months. A 5 wt. % aqueous solution (active polymer basis) of the Polyquaternium-11—acrylamide/DADMAC copolymer interjacent complex passed through a 100 mesh sieve (EW-59994-16, Cole-Parmer Instrument Company, Vernon Hills, IL) and left no insoluble polymer residue on the screen. The 5 wt. % solution was also measured for turbidity on a standard laboratory turbidimeter (Model 2100AN, Loveland, Col.) and measured less than 20 ntu.

EXAMPLE 3

The ingredients in Table 3 were added to a 2-Liter Resin Kettle fitted with a condenser, stirrer, thermocouple and nitrogen purge tube.

TABLE 3

| Ingredient | Charge (g) |
| --- | --- |
| Charge 1 | |
| Polyquaternium-28[7] | 156.7 |
| Deionized water | 97.4 |
| Charge 2 | |
| Sodium Hydroxide (50%) | 5.0 |
| 2-Acrylamido-2-methyl-2-propanesulfonic acid | 12.9 |
| Acrylic acid | 15.3 |
| Sodium Hydroxide (50%) | 11.7 |
| Acrylamide (50%) | 19.1 |
| Acryloyloxyethyl, trimethyl ammonium chloride (80.5%) | 70.3 |
| NaEDTA | 0.3 |
| Charge 3 | |
| Sodium persulfate | 0.2 |
| Deionized water | 6.0 |
| Charge 4 | |
| Deionized water | 6.0 |
| Sodium metabisulfite | 0.6 |
| Charge 5 | |
| Deionized water | 150.0 |
| Sodium metabisulfite | 1.5 |

[7]20 wt % aq. solution available as Gafquat ® HS-100 from International Specialty Products, Wayne, N.J.

Charge 1 was added to the Resin Kettle and mixed until uniform. Charge 2 was then added to the Resin Kettle an mixed until uniform. The pH should of the solution was about 5.1. The mixture was stirred with heating and a nitrogen sub-surface purge at about 3-5 scfh was begun for about 30 minutes. Charge 3 was added to the Resin Kettle wile stirring and about two minutes thereafter Charge 4 was added to the Resin Kettle.

In about two minutes, the solution temperature began to rise. After about three minutes, the nitrogen purge was reduced to a blanket headspace flow at about 0.5 scfh and the reaction temperature exceeded 80° C. After about one hour, charge 5 was added to the Resin Kettle, maintaining the temperature at 80° C. for at least 30 minutes. The solution remained uniform after standing at room temperature for three months. A 5 wt. % aqueous solution (active polymer basis) of the acrylic acid/AMPSA/acrylamide/AETAC copolymer—Polyquaternium-28 interjacent complex passed through a 100 mesh sieve (EW-59994-16, Cole-Parmer Instrument Company, Vernon Hills, Ill.) and left no insoluble polymer residue on the screen. The 5 wt. % solution was also measured for turbidity on a standard laboratory turbidimeter (Model 2100AN, Loveland, Col.) and measured less than 20 ntu.

EXAMPLE 4

A interjacent complex was prepared as in example 2 using the ingredients outlined in Table 4.

TABLE 4

| Ingredient | Charge (g) |
| --- | --- |
| Charge 1 | |
| Polyquaternium-10[8] | 35.1 |
| MEHQ | 0.0016 |
| Deionized water | 390.2 |
| Charge 2 | |
| Acrylamide (50%) | 20.4 |
| DADMAC (64.8%) | 30.6 |
| NaEDTA | 0.02 |
| Charge 3 | |
| 2,2'-Azobis(2-methylpropionamide)dihydrochloride | 0.4 |
| Deionized water | 7.5 |

TABLE 4-continued

| Ingredient | Charge (g) |
|---|---|
| Charge 4 | |
| Deionized water | 250.0 |

[8]Dry product available as Celquat ® SC-230M from National Starch and Chemical, Bridgewater, N.J.

The resulting interjacent complex solution contained 4.7% Polyquaternium-10 and 4.0% acrylamide-DADMAC copolymer. The solution had a Brookfield viscosity of 122,000cps measured using RV spindle No. 7 @ 10 rpm at 25° C. The solution remained uniform after standing at room temperature for three months. A 5 wt. % aqueous solution (active polymer basis) of the acrylamide/DADMAC copolymer—Polyquaternium-10 interjacent complex passed through a 100 mesh sieve (EW-59994-16, Cole-Parmer Instrument Company, Vernon Hills, Ill.) and left no insoluble polymer residue on the screen. The 5 wt. % solution was also measured for turbidity on a standard laboratory turbidimeter (Model 2100AN, Loveland, Col.) and measured less than 20 ntu.

EXAMPLE 5

A 50/25/25 w/w DADMAC/acrylamide/acrylic acid terpolymer (Polyquaternium-39) was prepared using the ingredients in Table 5 and the polymerization procedure of example 3.

TABLE 5

| Ingredient | Charge (g) |
|---|---|
| Charge 1 | |
| DADMAC (64.8%) | 92.4 |
| Acrylic acid | 31.7 |
| Sodium Hydroxide (50%) | 4.6 |
| acrylamide (50%) | 61.2 |
| Deionized water | 418.3 |
| NaEDTA | 0.03 |
| Charge 3 | |
| Sodium persulfate | 0.14 |
| Deionized water | 4.2 |
| Charge 4 | |
| Deionized water | 2.4 |
| Sodium metabisulfite | 0.02 |

The resulting polymer gel contained 19.8% polymer by weight. The terpolymer was used to make an interjacent complex using the polymerization method of example 3 and the ingredients listed in Table 6.

TABLE 6

| Ingredient | Charge (g) |
|---|---|
| Charge 1 | |
| Terpolymer described in Table 5 (19.8%) | 242.8 |
| Charge 2 | |
| Acrylamide (50%) | 60.5 |
| DADMAC (64.8%) | 46.5 |
| NaEDTA | 0.03 |

TABLE 6-continued

| Ingredient | Charge (g) |
|---|---|
| Charge 3 | |
| Sodium persulfate | 0.9 |
| Deionized water | 4.7 |
| Charge 4 | |
| Deionized water | 3.9 |
| Sodium metabisulfite | 0.02 |
| Charge 5 | |
| Deionized water | 390.0 |
| Sodium metabisulfite | 4.2 |

The resulting interjacent complex solution contained 6.3% of the terpolymer described in Table 5 and 7.9% of the acrylamide-DADMAC copolymer. The solution remained uniform after standing at room temperature for three months. A 5 wt. % aqueous solution (active polymer basis) of the acrylamide/DADMAC copolymer—Polyquaternium-39 interjacent complex passed through a 100 mesh sieve (EW-59994-16, Cole-Parmer Instrument Company, Vernon Hills, Ill.) and left no insoluble polymer residue on the screen. The 5 wt. % solution was also measured for turbidity on a standard laboratory turbidimeter (Model 2100 AN, Loveland, Col.) and measured less than 20 ntu.

EXAMPLE 6

An interjacent complex was prepared using the polymerization method described in example 2 and the ingredients in Table 7.

TABLE 7

| Ingredient | Charge (g) |
|---|---|
| Charge 1 | |
| Guar[9] | 5.0 |
| MEHQ[5] | 0.0016 |
| Deionized water | 455.2 |
| Charge 2 | |
| Acrylamide (50%) | 51.8 |
| Acryloyloxyethyl, trimethyl ammonium chloride (80.5%) | 67.3 |
| NaEDTA | 0.16 |
| Charge 3 | |
| 2,2'-Azobis(2-methylpropionamide)dihydrochloride[6] | 0.25 |
| Deionized water | 6.0 |
| Charge 4 | |
| Deionized water | 100.0 |
| Sodium metabisulfite | 1.0 |

[9]WG-22 available from PolyPro, Inc., Dalton, GA

The resulting interjacent complex solution contained 0.8% guar and 11.9% acrylamide-acryloyloxyethyl, trimethyl ammonium chloride copolymer. The solution remained uniform after standing at room temperature for three months. A 5 wt. % aqueous solution (active polymer basis) of the acrylamide/AETAC copolymer—guar interjacent complex passed through a 100 mesh sieve (EW-59994-16, Cole-Parmer Instrument Company, Ill.) and left no insoluble polymer residue on the screen. The 5 wt. % solution was also measured for turbidity on a standard laboratory turbidimeter (Model 2100AN, Loveland, Col.) and measured less than 20 ntu.

EXAMPLE 7

A interjacent complex was prepared using the polymerization method described in example 2 and the ingredients in Table 8.

TABLE 8

| Ingredient | Charge (g) |
| --- | --- |
| Charge 1 | |
| Xanthan gum[10] | 2.6 |
| MEHQ | 0.0016 |
| Deionized water | 457.6 |
| Charge 2 | |
| Acrylamide (50%) | 25.1 |
| Acryloyloxyethyl, trimethyl ammonium chloride (80.5%) | 65.7 |
| NaEDTA | 0.04 |
| Charge 3 | |
| 2,2'-Azobis(2-methylpropionamide) dihydrochloride[6] | 0.25 |
| Deionized water | 3.4 |
| Charge 4 | |
| Deionized water | 150.0 |
| Sodium metabisulfite | 0.5 |

[10]Flo-Vis-Plus, MI Drilling Fluids, Houston, TX.

The resulting interjacent complex solution contained 0.5% xanthan gum and 12.0% acrylamide-acryloyloxyethyl, trimethyl ammonium chloride copolymer. The solution remained uniform after standing at room temperature for three months. A 5 wt. % aqueous solution (active polymer basis) of the acrylamide/AETAC copolymer—xanthan gum interjacent complex passed through a 100 mesh sieve (EW-59994-16, Cole-Parmer Instrument Company, Vernon Hills, Ill.) and left no insoluble polymer residue on the screen. The 5 wt. % solution was also measured for turbidity on a standard laboratory turbidimeter (Model 2100 AN, Loveland, Col.) and measured less than 20 ntu.

EXAMPLE 8-14

The following physical blends of the polymers in Table 9 were prepared by adding 1:1 weight ratios of the respective polymer solutions to a suitable vessel equipped with an overhead mixer and mixing the solution until uniform.

TABLE 9

| Example No. | Polymer 1 | Polymer 2 |
| --- | --- | --- |
| 8 | Polyquaternium-7[1] | Polyquaternium-6[11] |
| 9 | Polyquaternium-11[4] | Polyquaternium-7[1] |
| 10 | Polyquaternium-28[7] | AMPS-acrylic acid-acrylamide-AETAC copolymer[12] |
| 11 | 10% aqueous solution of Polyquaternium-10[8] | Polyquaternium-7[13] |
| 12 | Polyquaternium-39[14] | Polyquaternium-7[15] |
| 13 | 2% aqueous solution of guar | Polyquaternium-33[16] |

TABLE 9-continued

| Example No. | Polymer 1 | Polymer 2 |
| --- | --- | --- |
| 14 | 1% aqueous solution of xanthan gum | Polyquaternium-33[17] |

[1]WSPQ7 available from WSP Chemicals & Technologies, Inc., Ambridge, Pa.
[4]20 wt % aqueous solution available as Gafquat® 755N from International Specialty Products, Wayne, N.J.
[7]20 wt % aqueous solution available as Gafquat® HS-100 from International Specialty Products, Wayne, N.J.
[8]Dry product available as Celquat® SC-230M from National Starch and Chemical, Bridgewater, N.J.
[11]prepared as described in example 1 without Polyquaternium-7 being present.
[12]prepared as described in example 3 without Polyquaternium-28 being present.
[13]prepared as described in example 4 without Polyquaternium-10 being present.
[14]prepared as described in example 5, Table 5.
[15]prepared as described in example 5, Table 6 without the polymer in Table 5 being present.
[16]prepared as described in example 6 without guar being present.
[17]prepared as described in example 7 without xanthan gum being present.

The solutions were allowed to stand at room temperature. After about 3 to 4 weeks, all of the solutions prepared in example 8-14 had formed two visibly distinct layers, i.e. they began to separate into two phases.

EXAMPLE 15

This example explains using the present water-soluble interjacent complexes to treat sludge. A jar test is performed utilizing an electrical variable speed beaker stir system, 500 ppm (on an active basis) of the interjacent complex of example 1 is added to 500 ml of a sludge from a thermophilic digestion system. The percentage of solids in the sludge is about 4.4 percent. The beaker is allowed to stir at 120 rpm for 30 seconds. At 30 seconds, the speed is reduced to 90 and after 15 seconds, the stir speed was slowed to 30 rpm and mixed for another 30 seconds. Large, heavy floc (e.g. with a diameter of at least about 4 mm) is formed with a somewhat cloudy supernatant.

EXAMPLE 16

This example explains using the present water-soluble interjacent complexes in paper-making. Drainage/Retention performance values are obtained using the Schopper-Reigler Freeness Test. The paper stock furnish is a 50:50 w/w blend of hardwood and softwood pulps which contains 13 wt. % clay, 2 wt. % $TiO_2$, 2 wt. % alum and 1 wt.% rosin. The interjacent complex of example 1 is added at 0.5 lb/ton on an active basis. Drainage and retention are improved compared to a control with no additive in the paper stock furnish.

EXAMPLE 17

A standard good quality flat paint is prepared using the ingredients in Table 10, including the interjacent complex of example 7 as a rheology modifier. The paint is prepared by standard paint-making methodology. In a typical process, the water, dispersants, thickeners, surfactants, defoamers and additives are charged to a high-speed dispersion mixer. Enough water is used to provide a viscosity which will give adequate shear to disperse the pigments. Pigments are added with good mixing and exposed to high shear for several minutes until a good dispersion is achieved. Following this, latex binder, thickeners, defoamers and coalescing solvent are added, along with enough water to achieve the desired paint viscosity for proper application.

TABLE 10

| Ingredient | weight (g) |
| --- | --- |
| Water | 380 |
| 28% ammonia water | 0.50 |
| Bactericide | 1.50 |
| Sodium polyacrylic acid | 8.0 |
| Disodium Phosphate | 2.0 |
| Nonylphenol ethoxylate surfactant | 3.0 |
| Defoamers | 6.0 |
| Calcined Kaolin | 182.3 |
| Magnesium silicate | 133.6 |
| Magnesium Aluminum Silicate | 4.0 |
| Rutile Titanium Dioxide | 168.0 |
| Interjacent complex of example 7 | 30.0 |
| Propylene glycol | 10.0 |
| Coalescing solvent | 10.0 |
| Poly vinyl acetate latex | 203.9 |

The present invention has been described with reference to specific details of particular embodiments thereof It is not intended that such details be regarded as limitations upon the scope of the invention except insofar as and to the extent that they are included in the accompanying claims.

We claim

1. A method of making paper comprising adding an interjacent complex to a pulp or a forming sheet, at a location on a paper machine, wherein the interjacent complex comprises:
    (a) a water-soluble polymer selected from the group consisting of water-soluble poly(meth)acrylates, water-soluble polyamides, water-soluble polyesters, water-soluble polyurethanes, water-soluble poly(vinyl amine), water-soluble poly(ethylene imine), water-soluble amine/epihalohydrin polyamines, water-soluble poly (meth)acrylamide, water-soluble (meth)acrylamide copolymers, water-soluble poly(meth)acrylic acid, water-soluble copolymers of (meth)acrylic acid, poly (diallyl dimethyl ammonium halides), copolymers of diallyl dimethyl ammonium halides, water-soluble vinyl pyrrolidone, water-soluble copolymers of vinyl pyrrolidone, poly(meth)acrylamidopropyltrimethyl ammonium halides, copolymers of (meth)acrylamidopropyltrimethyl ammonium halides, poly(meth) acryloyloxyethyltrimethyl ammonium halides, copolymers of (meth)acryloylmethyltrimethyl ammonium halides, poly(meth)acryloylmethyltrimethyl ammonium methyl sulfate, copolymers of (meth)acryloyloxyethyltrimethyl ammonium methyl sulfate, xanthan gums, sodium alginates, galactomanans, carageenan, gum arabic, hydroxyethyl cellulose, hydroxvoropyl cellulose, diallyl dimethyl ammonium chloride graft copolymers of hydroxyethylcellulose, polymeric quaternary ammonium salts of hydroxyethyl celluloses reacted with a trimethyl ammonium substituted epoxide, polymeric quaternary ammonium salts of hydroxyethyl celluloses reacted with lauryl dimethyl ammonium substituted epoxides, a quaternary ammonium derivative of hvdroxvpropvl guar and combinations thereof; and
    (b) one or more water-soluble monomers polymerized to form a polymer in the presence of the polymer in (a), wherein the water-soluble interjacent complex forms a solution in water that is free of insoluble polymer particles and maintains one uniform phase after standing at ambient conditions for at least three months.

2. The method of claim 1, wherein the monomers in (b) comprise a monomer mix comprised of (i) 0 to 100 mol % of one or more cationic monomers; (ii) 0 to 100 mol % of one or more anionic monomers; and (iii) 0 to 100 mol % of one or more nonionic monomers.

3. The method of claim 1, wherein the interjacent complex aids in forming the sheet and/or promotes dewatering of a formed sheet.

4. The method of claim 2, wherein the anionic monomer (ii) comprises one or more acid functional monomers selected from the group consisting of 2-acrylamido-2-methylpropane sulfonic acid, 2-methacrylamido-2-methylpropane sulfonic acid, sulfonated styrene, vinyl sulfonic acids, allyl ether sulfonic acids, (meth)acrylic acid, maleic acid, itaconic acid, N-(meth)acrylamidopropyl, N,N-dimethyl,amino acetic acid, N-(meth)acryloyloxyethyl, N,N-dimethyl,amino acetic acid, N-(meth)acryloyloxyethyl, N,N-dimethyl,amino acetic acid, crotonic acid, (meth)acrylamidoglycolic acid, and 2-(meth)acrylamido-2-methylbutanoic acid.

5. The method of claim 2, wherein the cationic monomer (i) comprises one or more carboxylic acid containing monomers selected from the group consisting of (meth)acrylamidopropyltrimethyl ammonium halides, (meth)acryloyloxyethyltrimethyl ammonium halides, poly(meth)acryloyloxyethyltrimethyl ammonium methyl sulfate, and diallyl dimethyl ammonium halides.

6. The method of claim 2, wherein the nonionic monomer (iii) comprises one or more selected from the group consisting of $C_1$-$C_{22}$ straight or branched chain alkyl or aryl (meth)acrylates, $C_1$-$C_{22}$ straight or branched chain N-alkyl or aryl (meth)acrylamide, (meth)acrylamide, N-methyl(meth)acrylamide, N-vinylpyrrolidone, vinyl acetate, ethoxylated (meth)acrylates, propoxylated (meth)acrylates, hydroxy functional (meth)acrylates, N,N-dimethyl(meth)acrylamide, styrene, $C_1$-$C_{22}$ straight or branched chain alkyl allyl ethers, and $C_1$-$C_{22}$ aryl allyl ethers.

7. The method of claim 2, wherein the monomer mix in (b) further comprises (iv) a branching quantity of one or more monomers that have two or more sites of reactive unsaturation.

8. The method of claim 1, wherein the reduced viscosity of the interjacent complex, as determined in a Ubbelhhde Capillary Viscometer at 0.05% by weight concentration of polymer in 1M NaCl solution, at 30° C., pH 7 ranges from 0.1 to 20 dl/g.

9. The method of claim 1, wherein the water-soluble polymer in (a) is one or more organic polymers selected from the group consisting of amine/epihalohydrin polyamines, poly (diallyldimethyl ammonium halides), poly(ethylene imines), poly(meth)acryloyloxyethyltrimethyl ammonium halides and poly(meth)acryloyloxyethyltrimethyl ammonium methyl sulfate; and the polymer in (b) is derived from polymerizing (meth)acrylamide and one or more monomers to provide a (meth)acrylamide copolymer.

10. The method of claim 9, wherein the (meth)acrylamide copolymer in (b) is anionic, nonionic, or cationic.

11. The method of claim 1, wherein the water-soluble polymer in (a) is a cationic polymer, and the monomer mix in (b) comprises acrylamide and the polymer formed in (b) is a high molecular weight acrylamide based polymer.

12. The method of claim 11, wherein the cationic polymer in (a) comprises one or more polymers selected from the group consisting of amine/epihalohydrin polyamines, poly (diallyldimethyl ammonium halides), poly(ethylenimines), poly(meth)acryloyloxyethyltrimethyl ammonium halides, and poly(meth)acryloyloxyethyltrimethyl ammonium methyl sulfate, and the acrylamide based polymer is an anionic, nonionic, or cationic polyacrylamide.

* * * * *